(12) United States Patent
McGuigan et al.

(10) Patent No.: US 7,019,135 B2
(45) Date of Patent: Mar. 28, 2006

(54) ANTI-VIRAL PYRIMIDINE NUCLEOSIDE ANALOGUES

(75) Inventors: Christopher McGuigan, Cardiff (GB); Jan Balzarini, Heverlee (BE); Erik De Clercq, Lovenjoel (BE)

(73) Assignees: University College Cardiff Consultants Limited, Cardiff (GB); Rega Foundation, Leuven (BE)

( * ) Notice: Subject to any disclaimer, the term of this patent is extended or adjusted under 35 U.S.C. 154(b) by 342 days.

(21) Appl. No.: 10/275,635

(22) PCT Filed: May 8, 2001

(86) PCT No.: PCT/GB01/02004

§ 371 (c)(1),
(2), (4) Date: Nov. 8, 2002

(87) PCT Pub. No.: WO01/85749

PCT Pub. Date: Nov. 15, 2001

(65) Prior Publication Data

US 2003/0176370 A1 Sep. 18, 2003

(30) Foreign Application Priority Data

May 9, 2000 (GB) .............................. 0011203

(51) Int. Cl.
*C07H 19/04* (2006.01)
*A61K 31/70* (2006.01)
*C07D 307/14* (2006.01)
*C07D 307/04* (2006.01)

(52) U.S. Cl. .................... 544/280; 544/278; 536/27.13; 514/265.1; 514/260; 514/260.1; 514/43

(58) Field of Classification Search ................ 544/280, 544/278; 536/27.13; 514/265.1, 260, 260.1, 514/43

See application file for complete search history.

(56) References Cited

FOREIGN PATENT DOCUMENTS

WO WO 98/49177 * 11/1998

OTHER PUBLICATIONS

Mauro Magnani et al., "Synthesis and targeted delivery of an azidothymidine homodinucleotide conferring protection to macrophages against retroviral infection", Proc. Nat'l. Acad. Sci. USA. vol. 93, pp. 4403–4408, Apr. 1996. Med. Sciences.*

Crisp, G.T., et al., "Palladium–catalyzed coupling of terminal alkynes with 5–(trifluoromethanesulfonyloxy) pyrimidine nucleosides," *J. Org. Chem.*, 1993, 58, 6614–6619.

Criuckshank, K.A., et al., "Oligonucleotide labeling: A concise synthesis of a modified thymidine phosphoramidite," *Tetrahedron Letters*, 1988, 29(41), 5221–5224.

De Clercq, E., et al., "Nucleic acid related compounds. 40. Synthesis and biological activities of 5–alkynyluracil nucleosides," *J. Med. Chem.*, 1983, 26, 661–666.

Inoue, H., et al., "Preparation of fluorescent nucleosides or nucleotides and their use for DNA hybridization probes," *Teljin Ltd., Japan*, (JP 62255499), 4 pages (abstract).

Inoue, H., et al., "Synthesis of dodecadeoxyribonucleotides containing a pyrrolo[2,3–d]pyrimidine nucleoside and their base–pairing ability," *Nippon Kagaku Kaishi*, 1987, ISSN: 0369–4577, 2 pages (abstract).

Kumar, R., et al., "Synthesis of 5–(1–azidovinyl) and 5–[2–(1–azirinyl)] analogs of 2'–deoxyuridine," *Can. J. Chem.*, 1996, 74, 1609–1615.

Kumar, H., et al., "Synthesis and properties of 5–(1, 2–dihaloethyl)–2'deoxyuridines and related analogues," *J. Heterocyclic Chem.*, 1991, 28, 1917–1925.

McGuigan, C., et al., "Potent and selective inhibition of varicella–zoster virus (VZV) by nucleoside analogues with an unusual bicyclic base," *J. Med. Chem.*, 1999, 42, XP–002177282, 4479–4484.

Robins, M.J., et al., "Nucleic acid related compounds. 39. Efficient conversion of 5–iodo to 5–alkynyl and derived 5–substituted uracil bases and nucleosides," *J. Org. Chem.*, 1983, 48, 1854–1862.

Robins M.J., et al., "Nucleic acid related compounds. 31. Smooth and efficient palladium–copper catalyzed coupling of terminal alkynes with 5–iodouracil nucleosides," *Tetrahedron Letters*, 1981, 22, 421–424.

Woo, J., et al., "G/C–modified oligodeoxynucleotides with selective complementarity: synthesis and hybridization properties," *Nucleic Acids Research*, 1996, 24(13), 2470–2475.

* cited by examiner

Primary Examiner—Paul V Ward
(74) Attorney, Agent, or Firm—Woodcock Washburn LLP

(57) ABSTRACT

Compounds of the general formula (I)

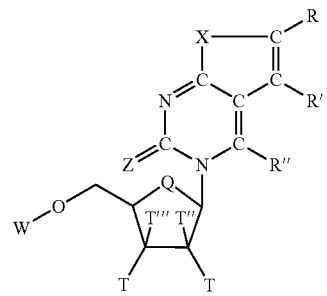

are described wherein R, R', R", Q, T, T', T", T"', W, X, and Z are as defined in the specification. Compounds according to the invention preferably display potent anti-viral activity against, for example, cytomegalo virus.

26 Claims, No Drawings

ANTI-VIRAL PYRIMIDINE NUCLEOSIDE ANALOGUES

The present invention relates to a new class of nucleoside analogues and to their therapeutic use in the prophylaxis and treatment of viral infection for example by cytomegalo virus (CMV). Cytomegalo virus is the aetiological agent in CMV retinitis and other viral infections, which can cause considerable human illness and suffering.

There has been considerable interest in the development of 5-substituted pyrimidine deoxynucleosides as putative antiviral agents.

WO 98/49177 describes a class of 5-substituted pyrimidine deoxynucleosides which demonstrate antiviral activity. A representative of the class of compounds disclosed is 3-(2'-deoxy-β-D-ribofuranosyl)-6-decyl-2,3-dihydrofuro[2,3-d]pyrimidin-2-one, which is said in WO 98/49177 to show potent anti-Varicella zoster virus (VZV) activity. The compound 6-(9-chlorononyl)-3-(4-hydroxy-5-(hydroxymethyl) tetrahydro-2-furanyl)-2,3-dihydrofuro[2,3,-d] pyrimidin-2-one is also described in WO 98/49177 and is said to demonstrate anti-CMV activity.

J. Med. Chem. 1999, 42, 4479, C. McGuigan, C. J. Yarnold, G. Jones, S. Velazquez, H. Barucki, A. Brancale, G. Andrei, R. Snoeck, E. de Clercq and J. Balzarini describes a series of 3-(2'-deoxy-β-D-ribofuransoyl)-2,3-dihydrofuro [2,3-d]pyrimidin-2-one compounds substituted at the 6-position with alkyl moieties of chain length varying from C5 to C12. Data is given demonstrating anti-VZV activity of the compounds. The same compounds are said on further evaluation to indicate, at 100 μM, a complete absence of anti-viral activity against CMV.

Tetrahedron Letters, 22, 421, 1981, M. J. Robins and P. J. Barr describes a method of coupling terminal alkynes with protected 5-iodouracil nucleotides in the presence of a catalyst to give the corresponding 5-(alkyn-1-yl) uracil nucleosides.

J. Med. Chem. 26, 661, 1983, E. de Clercq, J. Descamps, J. Balzarini, J. Giziewicz, P. J. Barr and M. J. Robins describes a catalytic process for coupling terminal alkynes with 5-iodo-1-(2,3,5,-tri-O-p-toluyl-β-D-arabinofuranosyl) uracil and 5-iodo-3',5'-di- O-p-toluyl-2'-deoxyuridine. A cyclized by-product having methyl substituted at the 6-position was isolated and characterised spectroscopically.

J. Org. Chem. 48, 1854, 1983, M. J. Robins and P. J. Barr describes catalytic coupling of terminal alkynes with 5-iodo-1-methyluracil and 5-iodouracil nucleotides protected as their p-toluyl esters. The article also describes the conversion of 5-hexynyl-2'-deoxyuridine to cyclized 6-n-butyl-3-(2-deoxy-β-D-erythro-pentofuraosyl)furano[2,3-d]pyrimidin-2-one.

Tetrahedron Letters 29, 5221, 1988, K. A. Cruickshank and D. L. Stockwell describes the catalytic condensation of 5'-dimethoxytrityl-5-iodo-2'-deoxyuridine with N-trifluoroacetypropargylamine and subsequent conversion to the 3'-phosphoramidite.

J. Heterocyclic Chem. 28, 1917, 1991, R. Kumar, E. E. Knaus and L. I. Wiebe describes a reaction employing 5-(1-fluoro-2-bromoethyl)-3',5'-di-O-acetyl-2'-deoxyuridine and producing a compound having the formula:

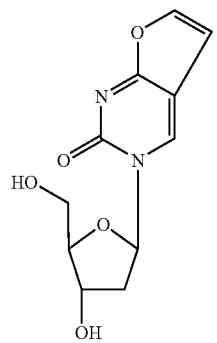

J. Org. Chem. 1993, 58, 6614, G. T. Crisp and B. L. Flynn describes palladium catalysed couplings of terminal alkynes with a variety of oxyuridines. One coupling described is that between 5-ethynyl-2'-deoxyuridine and a range of fluorinated aryl compounds.

Nucleic Acids Research 1996, 24, 2470, J. Woo, R. B. Meyer and H. B. Gamper describes a process for the preparation of 3-(2'-deoxy-β-D-ribofuranosyl)-pyrrolo-[2,3-d]-pyrimidine-2(3H)-one.

Can. J. Chem. 74, 1609, 1996, R. Kumar, L. I. Wiebe, E. E. Knaus describes a range of deoxyuridine compounds and their various anti-viral activity. A compound of the formula:

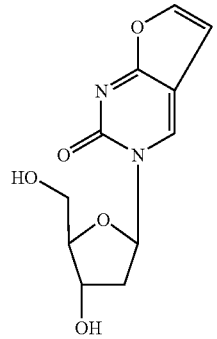

was found to be inactive in the vitro assays against HSV-1, HSV-2, VZV and CMV.

JP 62255499 (Teijin Ltd) describes the preparation of fluorescent nucleosides or nucleotides and their use for DNA hybridization probes. The compounds described have the general formula:

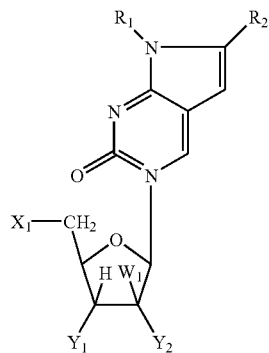

wherein $X_1$ and $Y_1$ are HO[P(O)(OH)O]n, $Z_1$ is H or HO[P(O)(OH)O]m, with m and n=0 to 3, W1 is H or HO and $R_1$ and $R_2$ are H or $C_1$ to $C_{10}$ alkyl.

Nippon Kagaku Kaishi 7, 1214, 1987 describes the synthesis of fluorescent dodecadeoxy ribonucleotides having the general formula:

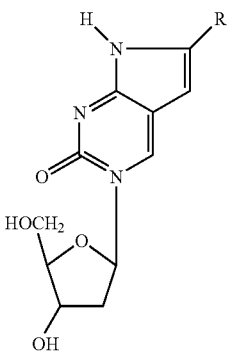

where R can be H or butyl.

It is an object of the present invention to provide a novel class of nucleoside analogues.

It is a further object of the present invention to provide a novel class of nucleoside analogues for therapeutic use in the prophylaxis and treatment of viral infection for example by cytomegalo virus.

According to a first aspect of the present invention there is provided a compound having formula I as follows:

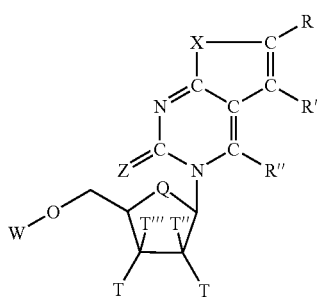

I wherein

R is selected from the group comprising, optionally substituted, $C_5$ to $C_{20}$ alkyl and, optionally substituted $C_5$ to $C_{20}$ cycloalkyl;

R' is selected from the group comprising hydrogen, alkyl, cycloalkyl, halogens, amino, alkylamino, dialkylamino, nitro, cyano, alkyoxy, aryloxy, thiol, alkylthiol, arylthiol, and aryl;

R" is selected from the group comprising hydrogen, alkyl, cycloalkyl, halogens, alkyloxy, aryloxy and aryl;

Q is selected from the group comprising O, NH, S, N-alkyl and $CY_2$, where Y may be the same or different and is selected from H, alkyl and halogens;

X is selected from the group comprising O, NH, S, Se, N-alkyl, $(CH_2)_n$ where n is 1 to 10, and $CY_2$, where Y may be the same or different and is selected from hydrogen, alkyl and halogens;

Z is selected from the group comprising O, S, NH and N-alkyl;

T is selected from the group comprising H, halogens, alkyl ($C_1$ to $C_{10}$), O-alkyl ($C_1$ to $C_{10}$), $N_3$ and CN;

T' is selected from the group comprising H, halogens, O-alkyl ($C_1$ to $C_{10}$), $N_3$ and CN;

or T and T' together form a bridge which is selected from the group comprising —O—, —NH— and —$(CH_2)_p$— wherein p is an integer from 1 to 6;

T" is selected from the group comprising H, OH, halogens, $N_3$ and CN;

T''' is selected from the group comprising H, OH, halogens, $N_3$ and CN;

or T" and T''' together form a bridge which is selected from the group comprising —O—, —NH— and —$(CH_2)_p$— wherein p is an integer from 1 to 6;

or T and T''' together form =$CH_2$; and

W is selected from the group comprising H, a phosphate group and a phosphonate group.

Essential to the present class of compounds is the presence of a saturated —CTT'"—CT'T"—bond, in which T is not OH, opposite Q in the Q-containing five membered ring. The compounds of the present invention are therefore dideoxy compounds. Preferably T is H. More preferably each of T, T', T" and T''' is H. Surprisingly, members of the present class of compounds can display potent anti-viral activity against CMV, but not against VZV.

The compounds of the present invention are therefore in direct contrast to the 2'-deoxy compounds as described in the J. Med. Chem. 1999, 42, 4479 reference mentioned above, which prior art compounds display potentially useful activity against VZV, but not against CMV.

Members of the present class of compounds of the present invention can moreover display potent anti-CMV activity at toxicity levels compatible with the use of the compounds as a drug to be administered to a patient.

As is well-known, a sugar moiety is capable of interacting directly with a strand of DNA. Although we do not wish to be bound by any theory, the absence of a sugar group as a substituent on the nucleoside group in the present compounds suggests that the mechanism by which they act against, for example, CMV will be different to that employed against VZV by the sugar group-containing compounds described in the above mentioned 1999 J. Med. Chem. article.

It is to be understood that the present invention extends to compounds according to formula I wherein the group W is modified to any pharmacologically acceptable salt or derivative of —H, phosphates or phosphonates. The present invention also includes any compound which is a pro-drug of the compound according to formula I, any such pro-drug being provided by modification of the moiety W, wherein W is selected from phosphates and derivatives thereof, and phosphonates and derivatives thereof.

Each of R, R' and R" may be substituted or unsubstituted and may be branched or unbranched. When any of R, R' and R" are alkyl or cycloalkyl, they may be saturated or unsaturated. "Alkyl" is therefore taken to include any aliphatic hydrocarbyl radical, including alkenyl and alkynyl groups, and "cycloalkyl" to include any cycloaliphatic hydrocarbyl radical, including alkenyl and alkynyl groups.

The nature, position and number of any substituents and unsaturation present in R, R' or R" may be varied.

Preferably R is an alkyl group. Preferably R is a straight chain alkyl group. Preferably R is an unsubstituted alkyl group. Preferably R is a saturated alkyl group.

Preferably R is a $C_7$ to $C_{13}$ alkyl group. More preferably R is a $C_8$ to $C_{12}$ alkyl group, even more preferably a $C_9$ to $C_{11}$ alkyl group. Particularly preferred is R being a $C_9$ or $C_{10}$ alkyl group.

Examples of suitable substituents on R include OH, halogens, amino, CN, COOH, $CO_2$alkyl($C_1$ to $C_5$), $CONH_2$, CONHalkyl($C_1$ to $C_5$), O-alkyl($C_1$ to $C_5$), SH, S-alkyl($C_1$ to $C_5$) and $NO_2$, and aryl(5 to 10 ring atoms), wherein said alkyl($C_1$ to $C_5$) and said aryl moieties are each optionally substituted.

Substituents on the said alkyl($C_1$ to $C_5$) moiety, which is preferably straight chain, can be selected from the group comprising OH, halogens, amino, CN, SH and $NO_2$, and is preferably a halogen, more preferably chlorine. Where the said alkyl moiety is $C_2$ to $C_5$, the substituent is preferably at the terminus position.

Substitutents on the said aryl moiety can be selected from the group comprising OH, halogens, amino, CN, $NO_2$, and $C_1$ to $C_{10}$ alkyl, which $C_1$ to $C_{10}$ alkyl moiety is optionally substituted with a member selected from the group comprising OH, halogens, amino, CN, SH, $NO_2$.

The said aryl moiety can comprise aryl or heteroaryl groups. Any ring heteroatoms may vary in position or number. Suitably 1, 2, 3 or 4 hetero ring atoms may be present, preferably selected, independently, from O, N and S. The said aryl moiety can comprise one, or two fused, 5, 6 or 7 membered rings. Suitably, where an aryl moiety is present in R, R in total can comprise, optionally substituted, —$(CH_2)_n$-aryl-$(CH_2)_m$H, where n is at least 5, m is at least 1, n+m≦10 and the aryl is preferably $C_6H_4$. Preferred aryl moieties present as a substituent in R include benzyl and heterosubstituted 5, 6 or 7 membered rings.

Where R is a straight chain alkyl group, a preferred position for substitution is the terminus position.

Suitably any substituent in R is non-polar, more suitably any such substituent is additionally hydrophobic. Preferred substituents on R include halogen and O-alkyl($C_1$ to $C_5$). Particularly preferred is O-alkyl with $C_4$, optionally terminally substituted with a halogen, preferably chlorine.

When R is a cycloalkyl group, it suitably comprises 5 to 12 ring carbon atoms arranged in one or two adjoining rings.

Suitably R' is selected from the group comprising H, $C_1$ to $C_{10}$ alkly, $C_3$ to $C_{10}$ cycloalkyl, $C_1$ to $C_{10}$ alkylamino, $C_1$ to $C_{10}$ dialkylamino, $C_1$ to $C_{10}$ alkyloxy, $C_6$ to $C_{10}$ aryloxy, $C_1$ to $C_{10}$ alkylthiol, $C_6$ to $C_{10}$ arylthiol and $C_6$ to $C_{10}$ aryl.

Suitably R" is selected from the group comprising H, $C_1$ to $C_{10}$ alkyl, $C_3$ to $C_{10}$ cycloakyl, $C_1$ to $C_{10}$ alkyloxy, $C_6$ to $C_{10}$ aryloxy and $C_6$ to $C_{10}$ aryl.

Preferably each of R' and R" is a small alkyl i.e. a $C_1$ to $C_2$ alkyl group or H. More preferably each of R' and R" is H.

Throughout the present specification "halogen" is taken to include any of F, Cl, Br and I.

Preferably Q is $CH_2$, S or O. More preferably Q is O. Where Q is N-alkyl, suitably the alkyl is $C_1$ to $C_5$ alkyl. Where Q is $CY_2$ and includes a halogen, the halogen is preferably fluorine.

Where Q is $CY_2$ and one or two of Y are alkyl, suitably the alkyl is $C_1$ to $C_5$ alkyl. Where Q is $CY_2$, Y is preferably H.

Preferably X is O, S or NH. More preferably X is O. Where X is $(CH_2)_n$, n is preferably 1 or 2, most preferably 1. Suitably when X is N-alkyl, alkyl is $C_1$ to $C_5$ alkyl. Suitably when X is $CY_2$, at least one Y is $C_1$ to $C_5$ alkyl. When X is $CY_2$ and each Y is alkyl, each alkyl is suitably $C_1$ to $C_5$.

Preferably Z is O. Where Z is N-alkyl, suitably the alkyl is $C_1$ to $C_5$ alkyl.

Preferably T" is selected from H, F, Cl, Br and OH, with each of T, T' and T'" being H, or preferably T" is selected from H, F, Cl and Br, with T' being selected from respectively H, F, Cl and Br, and T and T'" being H. Most preferably each of T, T', T"and T" ' is H.

Alternative preferred options include T' and T" each being F, with T and T'" each being H, and T'" being selected from F, Cl and Br, with each of T" and T' being selected from F, Cl, Br and OH, and T being H.

Where either of T and T' or T" and T'" together form a bridge, the bridge is preferably —O—. A bridge formed by T" and T'" is preferable, with T and T' each being H.

When W is a moiety which renders the compound a prodrug of the compound according to formula I it is to be understood that the term pro-drug includes the corresponding free base of each of the nucleosides described. The free base may moreover have direct antiviral action not dependent on metabolism to the corresponding nucleoside analogue.

It is also to be understood that "phosphate" includes diphosphates and triphosphates and "phosphonate" includes diphosphonates and triphosphonates. Hence W includes pharmacologically acceptable salts and derivatives of phosphates, diphosphates and triphosphates and of phosphonates, diphosphonates and triphosphonates. It also includes any moiety which provides a compound which is a pro-drug of the compound according to formula I, wherein W is selected from phosphates, diphosphates and triphosphates and derivatives thereof, and phosphonates, diphosphonates and triphosphonates and derivatives thereof.

Each compound may be the pure stereoisomer coupled at each of its chiral centres or it may be inverted at one or more of its chiral centres. It may be a single stereoisomer or a mixture of two or more stereoisomers. If it is a mixture the ratio may or may not be equimolar. Preferably the compound is a single stereoisomer. The compound may be in either enantiomeric form i.e. it may be either the D or L enantiomer either as a single stereoisomer or as a mixture of the two enantiomers. The D enantiomers are preferred.

It is to be understood that the present invention extends to compounds wherein the phosphate, if present, has been modified as well known to a person skilled in art.

Particularly preferred compounds embodying the present invention have the following formulae:

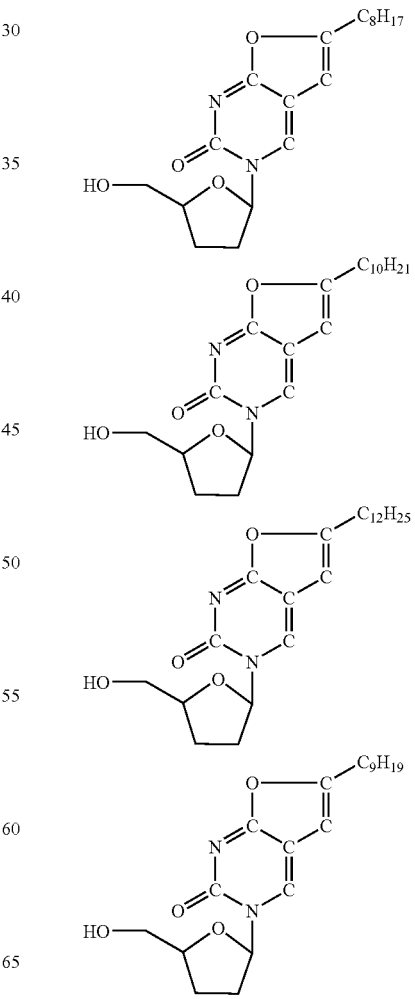

-continued

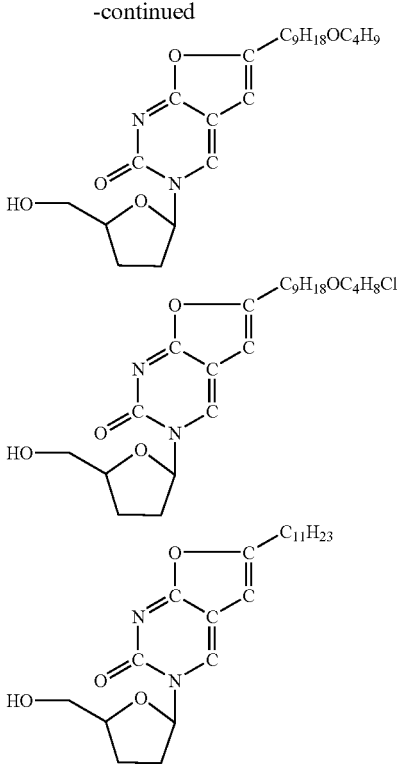

According to a further aspect of the present invention there is provided a method for preparing compounds having Formula I above wherein a 5-halo nucleoside analogue is contacted with a terminal alkyne in the presence of a catalyst. Alternatively 5-alkynyl nucleoside can be cyclised in the presence of a catalyst. Suitably the catalyst is a copper catalyst. The 5-alkynyl nucleoside has the general formula:

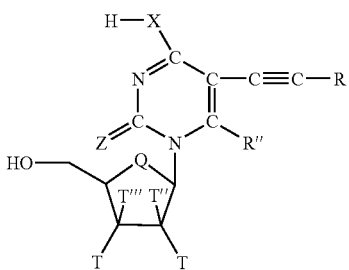

Compounds embodying the present invention can show anti-viral activity. In particular, it has surprisingly been found that compounds embodying the present invention can show antiviral activity against for example cytomegalo virus.

According to a further aspect of the present invention there is provided a compound according to the present invention for use in a method of treatment, suitably in the prophylaxis or treatment of a viral infection, preferably a cytomegalo viral infection.

According to a further aspect of the present invention there is provided use of a compound according to the present invention in the manufacture of a medicament for the prophylaxis or treatment of viral infection, preferably a cytomegalo viral infection.

According to a further aspect of the present invention there is provided a method of prophylaxis or treatment of viral infection, preferably a cytomegalo viral infection, comprising administration to a patient in need of such treatment an effective dose of a compound according to the present invention.

According to a further aspect of the present invention there is provided use of a compound of the present invention in the manufacture of a medicament for use in the prophylaxis or treatment of a viral infection, particularly an infection with cytomegalo virus.

According to a further aspect of the present invention there is provided a pharmaceutical composition comprising a compound of the present invention in combination with a pharmaceutically acceptable excipient.

According to a further aspect of the present invention there is provided a method of preparing a pharmaceutical composition comprising the step of combining a compound of the present invention with a pharmaceutically acceptable excipient.

The medicaments employed in the present invention can by administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of the recipient per day, preferably in the range of 1 to 25 mg per kilogram body weight per day and most preferably in the range 5 to 10 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Embodiments of the present invention will now be described by way of example only.

Experimental

In the following examples the bicyclic rings of the compounds are numbered following recommended IUPAC guidelines. Thus 3-(2'3'-dideoxy-ribo-β-D-furanosyl)-6-octyl-2,3-dihydrofuro[2,3-d]pyrimidin-2-one has the structure and is numbered as follows:

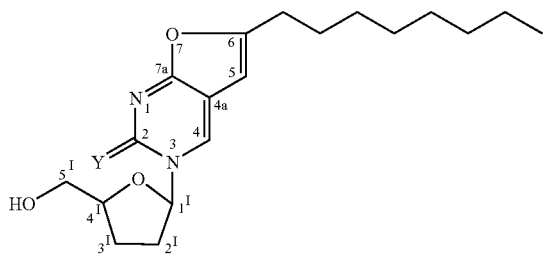

All $^1$H and $^{13}$C-NMR spectra were recorded on a Bruker Avance DPX300 spectrometer at 300 MHz and 75 MHz respectively. Chemical shifts were recorded in parts per million (ppm) downfield from tetramethylsilane.

Low resolution mass spectra were recorded on a Fisons Instruments VG Platform Electrospray mass spectrometer run in either positive or negative ion mode, with acetonitrile/water as the mobile phase.

EXAMPLES 1 to 9

Examples 1 to 9 each embody the present invention and illustrate the effect of chain length in the alkyl group R. In terms of Formula I above each compound had the following components X=O, Z=O, Q=O, T=T'=T"=T'''=H, W=H and R"=R'=H.

Example 1

3-[2',3'-dideoxy-ribo-β-D-furanosyl]-6-hexyl-2,3-dihydrofuro[2,3-d]pyrimidin-2-one

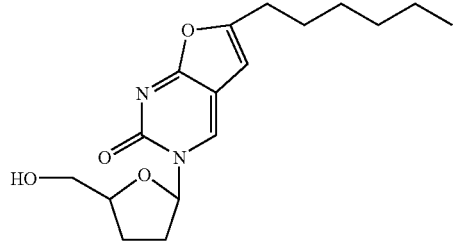

To a solution of 2',3'-dideoxy-5-iodouridine (350 mg, 1.035 mmol) in dry dimethylformamide (25 ml) at room temperature under $N_2$ atmosphere were added diisopropylethylamine (267 mg, 2.07 mmol, 2 eq, 0.36 ml), 1-octyne (342 mg, 3.106 mmol, 3 eq, 0.45 ml), tetrakis (triphenylphosphine) palladium (0) (120 mg, 0.104 mmol, 0.1 eq) and copper (1) iodide (39 mg, 0.206 mmol, 0.2 eq). The above reaction mixture was stirred at room temperature for 16 h under nitrogen. To the resulting solution copper (1) iodide (39 mg, 0.206 mmol, 0.2 eq) and triethylamine (10 ml) were added and the solution was heated to 70–80° C. for 6 h. Solvent was removed under high vacuum. Dichloromethane and methanol (1:1) 50 ml mixture was added to the above residue and to this solution an excess of Amberlite IRA-400 ($HCO_3^-$ form) was added and the resulting mixture was stirred at room temperature for 1 h. The resin was filtered, washed with methanol and the combined filtrate was evaporated to dryness to afford a dark brown residue. This was purified by flash column chromatography eluting with 6% methanol in ethyl acetate to afford a pale yellow oil (150 mg, 45%) which gave a white solid on trituration with ethyl acetate.

$^1$HNMR ($d_6$-DMSO): δ 8.82 (1H, S, H4), 6.40(1H, S, H-5), 5.98 (1H, m, H-1'), 5.19 (1H, t, J=5.3 Hz, 5'—OH), 4.15(1H, m, H-4'), 3.82(1H, m, H-5'), 3.63 (1H, m, H-5'), 2.62(2H, t, J=7.3 HZ, α-$CH_2$), 2.48 (1H, m, H-2'), 1.99 (1H, m, H-2'), 1.78 (2H, m, H-3'), 1.60–1.22 (8H, m, 4×$CH_2$), 0.83 (3H, t, J=6.9 Hz, $CH_3$).

$^{13}$CNMR ($d_6$-DMSO): δ 171.4(C-7a), 158.3(C-2), 154.1 (C-6), 137.3 (C4), 106.1 (C-4a), 100.1 (C-5), 88.3 (C-1'), 83.4 (C-4'), 61.6 (C-5'), 33.4 (C-2'), 31.2 (C-3'), 28.3, 27.6, 26.7, 23.9, 22.3 (5×$CH_2$), 14.2 (CH3)

MS (ES+), m/z 344 (10%, [MNa+1]$^+$), 343 (100%, [MNa]$^+$), 243 (15%, [Base Na]$^+$). $C_{17}H_{24}N2O_4$Na requires 343.1634, observed 343.1633.

Found: C, 63.51%; H, 7.70%; N, 8.71%. $C_{17}H_{24}N_2O_4$ requires: C, 63.73%; H, 7.55%; N, 8.74%.

Example 2

3-[2'3'-dideoxy-ribo-β-D-furanosyl]-6-octyl-2,3-dihydrofuro[2,3-d]pyrimidin-2-one

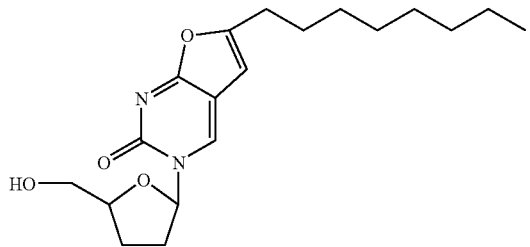

To a solution of 2',3'-dideoxy-5-iodouridine (400 mg, 1.18 mmol) in dry dimethylformamide (30 ml) at room temperature under $N_2$ atmosphere were added diisopropylethylamine (305 mg, 2.36 mmol, 2 eq, 0.41 ml), 1-decyne (491 mg, 3.55 mmol, 3 eq, 0.64 ml), tetrakis (triphenylphosphine) palladium (0) (136 mg, 0.117 mmol, 0.1 eq) and copper (1) iodide (45 mg, 0.236 mmol, 0.2 eq). The above reaction mixture was stirred at room temperature for 14 h under nitrogen. To the resulting solution copper (1) iodide (45 mg, 0.236 mmol, 0.2 eq) and triethylamine (10 ml) were added and the solution was heated to 70–80° C. for 6 hours. Solvent was removed under high vacuum. Dichloromethane and methanol (1:1) 50 ml mixture was added to the above residue and to this solution an excess of amberlite IPA-400 ($HCO_3^-$ form) was added and the resulting mixture was stirred at room temperature for 1 hour. The resin was filtered, washed with methanol and the combined filtrate was evaporated to dryness to afford a dark brown residue. This was purified by flash column chromatography eluting with 5% methanol in ethyl acetate to afford a pale yellow oil (140 mg, 42%) which gave a white solid on trituration with ethyl acetate.

$^1$HNMR ($d_6$-DMSO): δ 8.85 (1H, S, H-4), 6.43(1H, S, H-5), 6.01(1H, m, H-1'), 5.22(1H, t, J=5.1 Hz, 5'—OH), 4.18 (1H, m, H-4'), 3.84(1H, m, H-5'), 3.66 (1H, m, H-5'), 2.64 (2H, t, J=7.2 HZ, α-$CH_2$), 2.48 (1H, m, H-2'), 1.97 (1H, m, H-2'), 1.78 (2H, m, H-3'), 1.63–1.25 (12H, m, 6×$CH_2$), 0.85 (3H, t, J=6.9 Hz, $CH_3$).

$^{13}$CNMR ($d_6$-DMSO): δ 170.8(C-7a), 157.7(C-2), 153.5 (C-6), 136.7(C-4), 105.5 (C-4a), 99.4 (C-5), 87.7 (C-1'), 82.7 (C-4'), 61.0 (C-5'), 32.8 (C-2'), 30.9 (C-3), 28.3, 28.2, 28.0, 27.0, 26.0, 23.2, 21.7 (7×$CH_2$), 13.6 ($CH_3$)

MS(ES+), m/z 372 (15%,[MNa+1]$^+$), 371 (100%, [MNa]$^+$), 271 (20%, [Base Na]$^+$). $C_{19}H_{28}N_2O_4Na$ requires 371.1947, observed 371.1957

Found: C, 65.51%; H, 8.28%; N, 8.11%. $C_{19}H_{28}N_2O_4$ requires: C, 65.49%; H, 8.10%; N, 8.04%.

Example 3

3-[2',3'-dideoxy-ribo-β-D-furanosyl]-6-decyl-2,3-dihydrofuro[2,3-d]pyrimidin-2-one

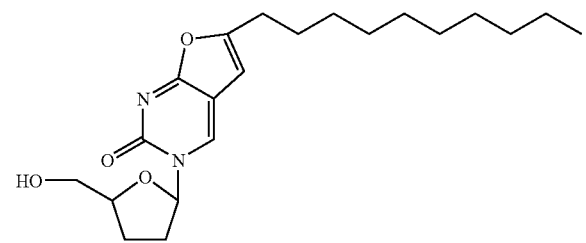

To a solution of 2'3'-dideoxy-5-iodouridine (400 mg, 1.18 mmol) in dry dimethylformamide (20 ml) at room temperature under $N_2$ atmosphere were added diisopropylethylamine (305 mg, 2.36 mmol, 2 eq, 0.41 ml), 1-dodecyne (588 mg, 3.54 mmol, 3 eq, 0.71 ml) tetrakis (triphenylphosphine) palladium (0) (136 mg, 0.117 mmol, 0.1 eq) and copper (1) iodide (45 mg, 0.236 mmol, 0.2 eq). The above reaction mixture was stirred at room temperature for 18 h under nitrogen. To the resulting solution copper (1) iodide (45 mg, 0.236 mmol, 0.2 eq) and triethylamine (10 ml) were added and the solution was heated to 70–80° C. for 8 h. Solvent was removed under high vacuum. Dichloromethane and methanol (1:1) 50 ml mixture was added to the above residue and to this solution an excess of amberlite IRA-400 ($HCO_3^-$ form) was added and the resulting mixture was stirred at room temperature for 1 h. The resin was filtered, washed with methanol and the combined filtrate was evaporated to dryness to afford a dark brown residue. This was purified by flash column chromatography eluting with 6% methanol in ethyl acetate to afford a pale yellow oil (360 mg, 81%) which gave a white solid on trituration with ethyl acetate.

$^1$H NMR ($d_3$-DMSO): δ 8.85(1H, S, H4), 6.43(1H, S, H-5), 6.01(1H, m, H-1'), 5.21(1H, t, J=5.2 Hz, 5'—OH), 4.18 (1H, m, H-4'), 3.84 (1H, m, H-5'), 3.65 (1H, m, H-5'), 2.64 (2H, t, J=7.3 Hz, α-$CH_2$), 2.48 (1H, m, H-2') 1.97 (1H, m, H-2'), 1.78 (2H, m, H-3'), 1.63–1.18(16H, m, 8×$CH_2$), 0.85 (3H, t, J=6.9 Hz, $CH_3$).

$^{13}$C NMR ($d_6$-DMSO): δ 171.4 (C-7a), 158.8 (C-2), 154.1 (C-6), 137.3, (C-4), 106.1 (C-4a), 100.1 (C-5), 88.3 (C-1'), 83.4 (C-4'), 61.6 (C-5'), 33.4 (C-2'), 31.6 (C-3'), 29.3, 29.0 28.6, 27.6, 26.7, 23.9, 22.4, (9×$CH_2$), 14.3 (CH3)

MS (ES+), m/z 399 (100%, [MNa]$^+$), 299 (50%, [BaseNa]$^+$).

$C_{21}H_{32}N_2O_4Na$ requires 399.2260, observed 399.2254

Found: C, 67.03%; H, 8.61%; N, 7.28%. $C_{21}H_{32}N_2O_4$ requires: C, 66.99%; H, 8.57%; N, 7.44%.

Example 4

3-[2',3'-dideoxy-ribo-β-D-furanosyl]-6-dodecyl-2,3-dihydrofuro[2,3-d]pyrimidin-2-one

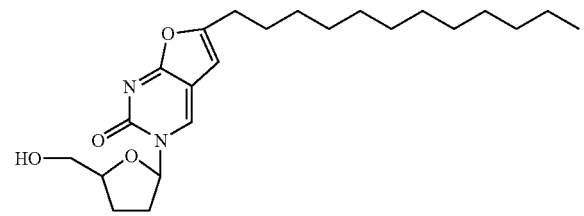

To a solution of 2',3'-dideoxy-5-iodouridine (350 mg, 1.035 mmol) in dry dimethylformamide (30 ml) at room temperature under $N_2$ atmosphere were added diisopropylethylamine (267 mg, 2.07 mmol, 2 eq, 0.36 ml), 1-tetradecyne (604 mg, 3.106 mmol, 3 eq, 0.76 ml), tetrakis (triphenylphosphine) palladium (0) (120 mg, 0.104 mmol, 0.1 eq) and copper (1) iodide (39 mg, 0.206 mmol, 0.2 eq). The above reaction mixture was stirred at room temperature for 18 h under nitrogen. To the resulting solution copper (1) iodide (39 mg, 0.206 mmol, 0.2 eq) and triethylamine (10 ml) were added and the solution was heated to 70–80° C. for 6 h. Solvent was removed under high vacuum. Dichloromethane and methanol (1:1) 50 ml mixture was added to the above residue and to this solution an excess of amberlite IRA-400 ($HCO_3^-$ form) was added and the resulting mixture was stirred at room temperature for 1 h. The resin was filtered, washed with methanol and the combined filtrate was evaporated to dryness to afford a dark brown residue. This was purified by flash column chromatography eluting with 6% methanol in ethyl acetate to afford a pale yellow oil (230 mg, 55%) which gave a white solid on trituration with diethyl ether.

$^1$H NMR ($d_6$-DMSO): δ 8.82 (1H, S, H-4), 6.41 (1H, S, H-5), 6.03 (1H, m, H-1'), 5.09(1H, bs, 5'—OH), 4.17 (1H, m, H-4'), 3.80 (1H, m, H-5'), 3.67 (1H, m, H-5'), 2.64 (2H, t, J=7.3 Hz, α-$CH_2$), 2.45 (1H, m, H-2'), 1.97 (1H, m, H-2'), 1.78 (2H, m, H-3'), 1.63–1.25(20H, m, 10×$CH_2$), 0.87 (3H, t, J=6.9 Hz $CH_3$).

$^{13}$C NMR ($d_3$-DMSO): δ 171.5 (C-7a), 158.4 (C-2), 154.2 (C-6), 137.2, (C-4), 106.2 (C-4a), 100.0 (C-5), 88.4 (C-1'), 83.2 (C-4'), 61.9 (C-5'), 33.3 (C-2'), 31.5 (C-3'), 29.2, 29.1, 28.9, 28.9, 28.6, 27.7, 26.7, 24.2, 22.3, (11×$CH_2$), 14.1 ($CH_3$).

MS (ES+), m/z 443 (5%, [MK]$^+$), 428 (20%, [MNa+H]$^+$), 427 (100%, [MNa]$^+$) 327(30%, [BaseNa]$^+$).

$C_{23}H_{36}N_2O_4Na$ requires 427.2573, observed 427.2575

Found: C, 68.53%; H, 9.07%; N, 6.84%. $C_{23}H_{36}N_2O_4$ requires: C, 68.29%; H, 8.97%; N, 6.92%.

Example 5

3-[2',3'-dideoxy-ribo-β-D-furanosyl]-6-tetradecyl-2,3-dihydrofuro[2,3-d]pyrimidin-2-one

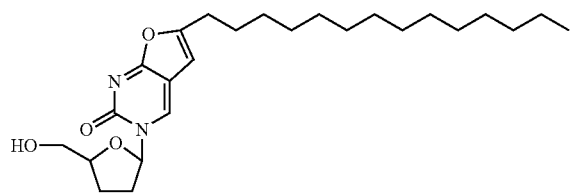

To a solution of 2',3'-dideoxy-5-iodouridine (350 mg, 1.035 mmol) in dry dimethylformamide (25 ml) at room temperature under $N_2$ atmosphere were added diisopropylethyl amine (267 mg, 2.07 mmol, 2 eq, 0.36 ml), 1-hexadecyne (690 mg, 3.106 mmol, 3 eq, 0.86 ml), tetrakis(triphenylphosphine) palladium (0) (120 mg, 0.104 mmol, 0.1 eq) and copper (1) iodide (39 mg, 0.206 mmol, 0.2 eq). The above reaction mixture was stirred at room temperature for 16 h under nitrogen. To the resulting solution copper (1) iodide (39 mg, 0.206 mmol, 0.2 eq) and triethylamine (10 ml) were added and the solution was heated to 70–80° C. for 8 hours. Solvent was removed under high vacuum. Dichloromethane and methanol (1:1) 50 ml mixture was added to the above residue and to this solution an excess of amberlite IRA-400 ($HCO_3^-$ form) was added and the resulting mixture was stirred at room temperature for 1 h. The resin was filtered, washed with methanol and the combined filtrate was evaporated to dryness to afford a dark brown residue. This was purified by flash column chromatography eluting with 5% methanol in ethyl acetate to afford an off white solid (250 mg, 56%).

$^1$HNMR (CDCl$_3$): δ 8.74 (1H, S, H-4), 6.25(1H, m, H-1'), 6.17 (1H, S, H-5), 4.34 (1H, m, H-4'), 4.21 (1H, m, H-5'), 3.94 (1H, m, H-5'), 2.68 (2H, t, J=7.7 Hz, α-CH$_2$), 2.56 (1H, m, H-2'), 2.56 (1H, m, H-2'), 2.23 (1H, m, H-2'), 1.99 (2H, m, H-3') 1.76–1.30 (24H, m, 12×CH$_2$), 0.93 (3H, t, J=6.9 Hz, CH3).

$^{13}$CNMR (CDCl$_3$): δ 172.1 (C-7a), 159.9(C-2), 155.4 (C-6), 136.1(C-4), 107.6 (C-4a), 99.4 (C-5), 89.3 (C-1'), 83.2 (C-4'), 63.3 (C-5'), 34.1 (C-2'), 32.3 (C-3'), 30.0, 30.0, 29.9, 29.7, 29.7, 29.4, 28.7, 27.2, 24.2, 23.1 (13×CH$_2$), 14.5 (CH3)

MS (ES+), m/z 471 (5%, [MK]$^+$), 456 (20%, [MNa+1]$^+$), 455 (100%, [MNa]$^+$), 355(40%, [BaseNa]$^+$).

$C_{25}H_{40}N_2O_4$Na requires 455.2886, observed 455.2881

Found: C, 69.43%; H, 9.46%; N, 6.47%. $C_{25}H_{40}N_2O_4$ requires: C, 69.41%: H, 9.32%; N, 6.48%.

Example 6

3-[2',3'-dideoxy-ribo-β-D-furanosyl]-6-nonyl-2,3-dihydrofuro[2,3-d]pyrimidin-2-one

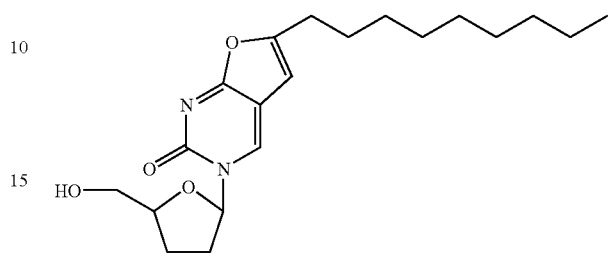

To a solution of 2',3'-dideoxy-5-iodouridine (300 mg, 0.887 mmol) in dry dimethylformamide (20 ml) at room temperature under $N_2$ atmosphere were added diisopropylethyl amine (229 mg, 1.775 mmol, 2 eq, 0.30 ml), 1-undecyne (405 mg, 2.662 mmol, 3 eq, 0.52 ml), tetrakis(triphenylphosphine) palladium (0) (102 mg, 0.887 mmol, 0.1 eq) and copper (1) iodide (34 mg, 0.177 mmol, 0.2 eq). The above reaction mixture was stirred at room temperature for 16 h under nitrogen. To the resulting solution copper (1) iodide (34 mg, 0.177 mmol, 0.2 eq) and triethylamine (10 ml) were added and the solution was heated to 70–80° C. for 4 h. Solvent was removed under high vacuum. Dichloromethane and methanol (1:1) 50 ml mixture was added to the above residue and to this solution an excess of amberlite IRA-400 ($HCO_3^-$ form) was added and the resulting mixture was stirred at room temperature for 1 h. The resin was filtered, washed with methanol and the combined filtrate was evaporated to dryness to afford a dark brown residue. This was purified by flash column chromatography eluting with 7% methanol in ethyl acetate to afford a pale yellow oil (138 mg, 52%) which gave a white solid on trituration with diethyl ether.

$^1$HNMR (CDCl$_3$): δ 8.76 (1H, S, H-4), 6.25 (1H, m, H-1'), 6.18 (1H, S, H-5) 4.34 (1H, m, H-4'), 4.18 (1H, m, H-5'), 3.94 (1H, m, H-5'), 2.68 (3H, m, α-CH$_2$+H-2'), 2.22 (1H, m, H-2') 1.99 (2H, m, H-3'), 1.74–1.11 (14H, m, 7×CH$_2$), 0.93 (3H, t, J=6.9 Hz, CH$_3$).

$^{13}$C NMR (CDCl$_3$): δ 172.1(C-7a), 159.8(C-2), 155.5 (C-6), 136.6(C-4), 107.6 (C-4a), 99.6 (C-5), 89.4 (C-1'), 83.5 (C-4'), 63.0 (C-5') 36.9 (C-2'), 34.2 (C-3'), 32.2, 29.8, 29.7, 29.4, 28.6, 27.2, 24.2, 23.0 (8×CH$_2$), 14.5 (CH$_3$)

MS (ES+), m/z 386 (15%, [MNa+1]$^+$), 385 (100%, [MNa]$^+$), 285(40%,[BaseNa]$^+$), $C_{20}H_{30}N_2O_4$Na requires 385.2103, observed 385.2104.

Found: C, 61.66%; H, 8.69%; N, 7.08%. $C_{20}H_{30}N_2O_4$·1.5 $H_2O$ requires: C, 61.67%; 8.54%; N, 7.19%.

Example 7

3-[2',3'-dideoxy-ribo-β-D-furanosyl]-6-undecyl-2,3-dihydrofuro[2,3-d]pyrimidin-2-one

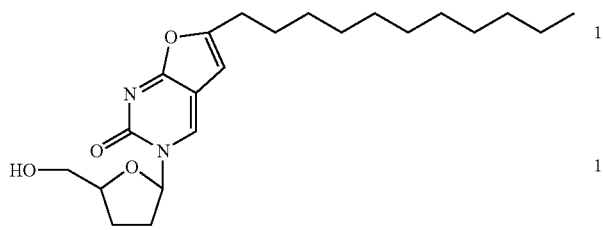

To a solution of 2',3'-dideoxy-5-iodouridine (250 mg, 0.739 mmol) in dry dimethylformamide (20 ml) at room temperature under $N_2$ atmosphere were added diisopropylethylamine (190 mg, 1.479 mmol, 2 eq, 0.41 ml), 1-tridecyne (400 mg, 2.218 mmol, 3 eq), tetrakis(triphenylphosphine) palladium (0) (85 mg, 0.074 mmol, 0.1 eq) and copper (1) iodide (28 mg, 0.148 mmol, 0.2 eq). The above reaction mixture was stirred at room temperature for 1 h under nitrogen. To the resulting solution copper (1) iodide (28 mg, 0.148 mmol, 0.2 eq) and triethylamine (10 ml) were added and the solution was heated to 70–80° C. for 4 h. Solvent was removed under high vacuum. Dichloromethane and methanol (1:1) 50 ml mixture was added to the above residue and to this solution an excess of amberlite IRA-400 ($HCO_3^-$ form) was added and the resulting mixture was stirred at room temperature for 1 h. The resin was filtered, washed with methanol and the combined filtrate was evaporated to dryness to afford a dark brown residue. This was purified by flash column chromatography eluting with 6% methanol in ethyl acetate to afford an off white solid (145 mg, 50%).

$^1$H NMR ($CDCl_3$): δ 8.74 (1H, S, H-4), 6.25 (1H, m, H-1'), 6.17 (1H, S, H-5), 4.34 (1H, m, H-4'), 4.21 (1H, m, H-5'), 3.94 (1H, m, H-5'), 2.68 (2H, t, J=7.5 Hz, α-$CH_2$), 2.53 (1H, m, H-2') 2.28 (1H, m, H-2'), 1.99 (2H, m, H-3'), 1.74–1.13 (18H, m, 9×$CH_2$), 0.93 (3H, t, J=6.9 Hz, $CH_3$).

$^{13}$CNMR ($CDCl_3$): δ 172.1 (C-7a), 159.8 (C-2), 155.5 (C-6), 136.6, (C-4), 107.6 (C-4a), 99.5 (C-5), 89.4 (C-1'), 83.4 (C-4'), 63.0 (C-5'), 34.2 (C-2'), 32.3 (C-3'), 30.0, 29.9, 29.7, 29.7, 29.4, 28.6, 27.2, 24.2, 23.1 (10×$CH_2$).

MS (ES+), m/z 429 (5%, [MK]$^+$), 414 (15%, [MNa+1]$^+$), 413(80%,[MNa]$^+$), 313(100%, [BaseNa]$^+$), 291(20%, [Base+1]$^+$).

Found: C, 59.18%; H, 9.09%; N, 6.55%. $C_{22}H_{34}N_2O_4$. 3$H_2O$ requires: C, 59.27%; H, 9.18%; N, 6.48%.

Example 8

3-(2'-3'-Dideoxy-β-D-ribofuranosyl)-6-[9-butyloxynonyl]-2,3-dihydrofuro[2,3-d]pyrimidin-2-one

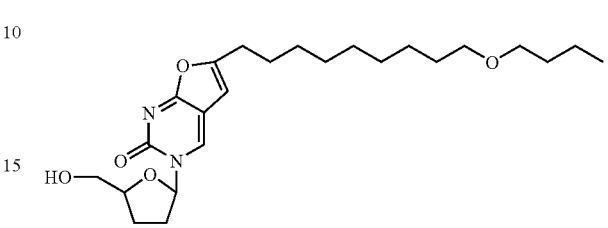

$C_{24}H_{38}N_2O_5$
Mol. Wt.: 434.57

To a stirred solution of 5-iodo-2'-3'-dideoxyuridine (95 mg, 0.282 mmol) in dry dimethylformamide (1 ml), at room temperature under a nitrogen atmosphere, was added diisopropylethylamine (73 mg, 0.10 ml, 0.564 mmol), 11-butyloxy-1-undecyne (189.5 mg, 0.846 mmol), tetrakis(triphenylphosphine) palladium(0) (32.62 mg, 0.028 mmol) and copper (I) iodide (10.75 mg, 0.056 mmol). The reaction mixture was stirred at room temperature for 19 hours, after which time copper (I) iodide (10 mg), triethylamine (2 ml) and methanol (3 ml) were added. The reaction mixture was then heated to 75° C. and stirred for 4 hours. The reaction mixture was concentrated in vacuo. The resulting residue was dissolved in dichloromethane/methanol (1:1) (6 ml) and an excess of Amberlite IRA-400 ($HCO_3^-$form) was added and the mixture was stirred for 30 minutes. The resin was filtered, washed with methanol and the combined filtrate was evaporate to dryness. The crude product purified by silica column chromatography, using an initial eluent of ethylacetate, followed by an eluent of ethylacetate/methanol (9:1). The appropriate fractions were combined and the solvent removed in vacuo, yielding the pure product as white solid (43 mg, 35% yield).

$^1$H-nmr ($d_6$-DMSO; 300 MHz): 8.86 (1H, s, H-4), 6.43 (1H, s, H-5), 6.00 (1H, dd, H-1'), 5.23 (1H, t, $^3$J=5.1 Hz, 5'—OH), 4.16 (1H, m, H-4'), 3.83 (1H, m, H-5'a), 3.64 (1H, m, H-5'b), 3.34 (4H, m, C$\underline{H}_2$OC$\underline{H}_2$), 2.64 (2H, t, $^3$J=6.9 Hz, α-$CH_2$), 2.43 and 2.00 (2H, m, H-2'a and H-2'b), 1.85 (2H, m, H-3'), 1.61–1.28 (18H, m, 9×$CH_2$), 0.87 (3H, t, $^3$J=6.8 Hz). $^{13}$C-nmr ($d_6$-DMSO; 75 MHz): 14.1 ($CH_3$), 19.3, 23.9, 26.0, 26.7, 27.7, 28.7, 29.0, 29.1, 29.2, 29.6, 31.7, 33.5 (12×$CH_2$, C-2' and C-3'), 61.7 (C-5'), 69.9, 70.3 (C$\underline{H}_2$O C$\underline{H}_2$), 83.5, 88.4 (C-1' and C-4'), 100.1 (C-5), 106.2 (C-4a), 137.4 (C-4), 154.2 (C-2), 158.4 (C-6), 171.5 (C-7a). Mass spectrum (ES-MS (+ve)); m/z 457 (100%, [M+Na]$^+$). FAB m/e 457.2673 (MNa$^+C_2H_{38}N_2O_5$Na requires 457.2678).

Example 9

3-(2'-3'-Dideoxy-β-D-ribofuranosyl)-6-[9-(4-chlorobutoxy)nonyl]-2,3-dihydrofuro[2,3-d]pyrimidin-2-one

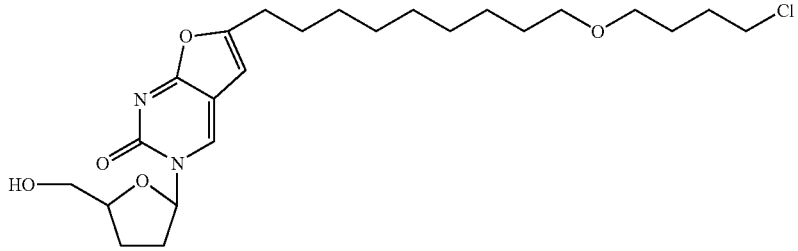

$C_{24}H_{37}ClN_2O_5$
Mol. Wt.: 469.01

To a stirred solution of 5-iodo-2'-3'-dideoxyuridine (95 mg, 0.282 mmol) in dry dimethylformamide (1 ml), at room temperature under a nitrogen atmosphere, was added diisopropylethylamine (73 mg, 0.10 ml, 0.564 mmol), 11-(4-chloro-butoxy)-1-undecyne (281.18 mg, 0.846 mmol), tetrakis(triphenylphosphine) palladium(0) (32.62 mg, 0.028 mmol) and copper (I) iodide (10.75 mg, 0.056 mmol). The reaction mixture was stirred at room temperature for 19 hours, after which time copper (I) iodide (10 mg), triethylamine (2 ml) and methanol (3 ml) were added. The reaction mixture was then heated to 75° C. and stirred for 4 hours. The reaction mixture was concentrated in vacuo. The resulting residue was dissolved in dichloromethane/methanol (1:1) (6 ml) and an excess of Amberlite IRA-400 ($HCO_3^-$ form) was added and the mixture was stirred for 30 minutes. The resin was filtered, washed with methanol and the combined filtrate was evaporate to dryness. The crude product purified by silica column chromatography, using an initial eluent of ethylacetate, followed by an eluent of ethylacetate/methanol (9:1). The appropriate fractions were combined and the solvent removed in vacuo, yielding the pure product as white solid (53 mg; 40% yield).

$^1$H-nmr ($d_6$-DMSO; 300 MHz): 8.86 (1H, s, H-4), 6.43 (1H, s, H-5), 6.00 (1H, dd, H-1'), 5.22 (1H, t, $^3J=5.2$ Hz, 5'—OH), 4.15 (1H, m, H-4'), 3.83 (1H, m, H-5'a), 3.64 (3H, m, H-5'b and C$\underline{H}_2$Cl), 3.35 (4H, m, C$\underline{H}_2$OC$\underline{H}_2$), 2.64 (2H, t, $^3J=7.1$ Hz, α-CH$_2$), 2.43 and 1.98 (2H, m, H-2'a and H-2'b), 1.85–1.27 (18H, m, 12×CH$_2$). $^{13}$C-nmr ($d_6$-DMSO; 75 MHz): 23.9, 26.0, 26.7, 26.9, 28.7, 28.9, 29.1, 29.2, 29.3, 29.4, 29.5, 33.5 (10×CH$_2$, C-2' and C-3'), 45.7 (C$\underline{H}_2$Cl), 61.6 (C-5'), 69.4, 70.3 (C$\underline{H}_2$OC$\underline{H}_2$), 83.4, 88.4 (C-1' and C-4'), 100.1 (C-5), 106.2 (C-4a), 137.3 (C-4), 154.2 (C-2), 158.4 (C-6), 171.5 (C-7a). Mass spectrum (ES-MS (+ve)); m/z 491 (100%, [M+Na]$^+$). FAB mn/e 491.2180 (MNa$^+$ $C_{24}H_{37}N_2O_5$ClNa requires 491.2289).

Biological Activity

Each of the products of Examples 1 to 9 was tested in vitro in tissue cultures for toxicity and for potent antiviral actions with respect to cytomegalo virus (CMV). The results are given in Table I below.

The column headings in Table I are as follows:

R represents R as in formula I.

EC50/μM CMV-AD169 is the drug concentration in μM required to reduce by 50% CMV strain AD169 induced cytopathicity in human embryonic lung fibroblast (HEL) cells measured 7 days post infection compared to untreated control.

EC50/μM CMV Davis is the drug concentration in μM required to reduce by 50% CMV strain Davis induced cytopathicity in human embryonic lung fibroblast (HEL) cells measured 7 days post infection compared to untreated control.

MCC/μM is the minimum cytotoxic concentration to human embryonic lung cells.

CC50/μM is the compound concentration required to reduce the cell number by 50%.

Further details of the methodology employed can be found in McGuigan et al. J. Med. Chem., 1999, 42, 4479–4484.

TABLE II

| Example.-R | EC50/μM CMV-AD169 | EC50/μM CMV-Davis | MCC/μM | CC50/μM |
|---|---|---|---|---|
| 1.-nC$_6$H$_{13}$ | 32 | >50 | 200 | 143 |
| 2.-nC$_8$H$_{17}$ | 1.5 | 2.4 | 20 | 112 |
| 6.-nC$_9$H$_{19}$ | 1.2 | 1.3 | 200 | >200 |
| 8.-nC$_9$H$_{18}$OC$_4$H$_9$ | 1.2 | 1.0 | 5 | 200 |
| 9.-nC$_9$H$_{18}$OC$_4$H$_8$Cl | 2.6 | 1.0 | 20 | >200 |
| 3.-nC$_{10}$H$_{21}$ | 2.6 | 3.2 | >200 | >200 |
| 7.-nC$_{11}$H$_{23}$ | 1.4 | 1.2 | 50 | >200 |
| 4.-nC$_{12}$H$_{25}$ | 3.7 | 5.0 | 200 | >200 |
| 5.-nC$_{14}$H$_{29}$ | 25 | 40 | 200 | >200 |
| Ganciclovir | 2.6 | 3.4 | >150 | Nd |

Ganciclovir is a commercially available drug currently regarded as the drug of choice for treating a patient having a cytomegalo virus infection. Ganciclovir has the structure:

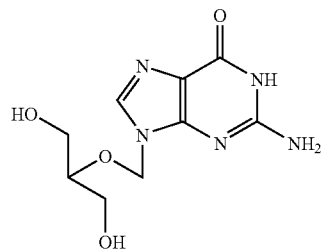

The equivalent data for Ganciclovir by way of comparison are included in Table I.

As can be seen from the data given in Table I, the compounds of Examples 2, 6, 7, 8 and 9 showed potent anti-CMV activity and the compounds of Examples 3 and 4 demonstrated anti-CMV activity at least comparable to that of the known drug Ganciclovir. The compounds of Examples 2, 7, 8 and 9, however, demonstrated toxicity greater than any of the compounds of Examples 1, 3, 4, 5 and 6.

The compounds of Examples 3, 4 and 6 wherein R is, respectively, $nC_{10}H_{21}$, $nC_{12}H_{25}$ and $nC_9H_{19}$ demonstrated anti-CMV potency in the present assays at least comparable to that of the known drug Ganciclovir in combination with an acceptable level of toxicity.

The compound of Example 3 wherein R is $-nC_{10}H_{21}$ was tested to assess its potency against VZV. Employing the equivalent EC50 assay as set out above, namely a measurement of the drug concentration required to reduce by 50% the VZV induced cytopathicity in human embryonic fibroblast (HEL) measured 7 days post infection, a concentration of 40 μM was found with respect to VZV OKA strain and a concentration of 20 μM was measured with respect to VZV YS strain. The compound of Example 3 is therefore seen to be substantially more active against CMV, than against VZV.

What is claimed is:

1. A compound having the formula:

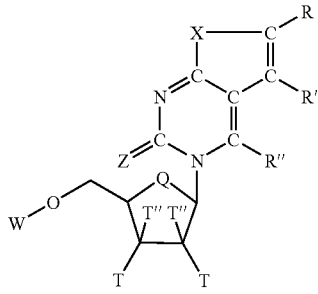

wherein:
R is selected from the group consisting of optionally substituted $C_5$ to $C_{20}$ alkyl and optionally substituted $C_5$ to $C_{20}$ cycloalkyl, wherein said optional substituents are selected from the group consisting of OH, halogens, amino, CN, COOH, $CO_2R^1$, $CONH_2$, $CONHR^2$, $OR^3$, SH, $SR^4$, $NO_2$, and aryl (5 to 10 ring atoms) optionally substituted with a member selected from the group consisting of OH, halogens, amino, CN, $NO_2$, and $C_1$ to $C_{10}$ alkyl, which $C_1$ to $C_{10}$ alkyl moiety is optionally substituted with a member selected from the group consisting of OH, halogens, amino, CN, SH and $NO_2$;
R' is selected from the group consisting of hydrogen, alkyl, cycloalkyl, halogens, amino, alkylamino, dialkylamino, nitro, cyano, alkyloxy, aryloxy, thiol, alkylthiol, arylthiol, and aryl;
R" is selected from the group consisting of hydrogen, alkyl, cycloalkyl, alkyloxy, aryloxy and aryl;
$R^1$, $R^2$, $R^3$ and $R^4$ are each independently selected from the group consisting of optionally substituted $C_1$ to $C_5$ alkyl, wherein said optional substituents are selected from the group consisting of OH, halogens, amino, CN, SH and $NO_2$;
Q is selected from the group consisting of O, NH, S, N-alkyl and $CY_2$, where Y may be the same or different and is selected from the group consisting of H, alkyl and halogens;
X is selected from the group consisting of O, NH, S, Se, N-alkyl, $(CH_2)_n$ where n is 1 to 10, and $CY_2$ where Y may be the same or different and is selected from hydrogen, alkyl and halogens;
Z is selected from the group consisting of O, S, NH, and N-alkyl;
T is selected from the group consisting of H, halogens, alkyl ($C_1$ to $C_{10}$), O-alkyl ($C_1$ to $C_{10}$), $N_3$ and CN;
T' is selected from the group consisting of H, halogens, O-alkyl ($C_1$ to $C_{10}$), $N_3$ and CN;
or T and T' together form a bridge which is selected from the group consisting of —O—, —NH— and —$(CH_2)_p$— wherein p is an integer from 1 to 6;
T" is selected from the group consisting of H, OH, halogens, $N_3$ and CN;
T'" is selected from the group consisting of H, OH, halogens, $N_3$ and CN;
or T" and T'" together form a bridge which is selected from the group consisting of —O—, —NH— and —$(CH_2)_p$— wherein p is an integer from 1 to 6;
or T and T'" together form $=CH_2$; and
W is selected from the group consisting of H, a phosphate group and a phosphonate group;
and a pharmacologically acceptable salt, or pro-drug thereof.

2. A compound according to claim 1 wherein R is a straight chain alkyl group.

3. A compound according to claim 1 wherein R is an unsubstituted alkyl group.

4. A compound according to claim 1 wherein $R^1$, $R^2$, $R^3$ and $R^4$ are each independently selected from the group consisting of optionally substituted $C_2$ to $C_5$ alkyl, wherein said optional substituent is at the terminus position.

5. A compound according to claim 1 wherein R is substituted with O-alkyl($C_1$ to $C_5$), the $C_1$ to $C_5$ alkyl moiety portion of which is optionally substituted with a halogen.

6. A compound according to claim 1 wherein R is a straight chain alkyl group and is substituted at the terminus position.

7. A compound according to claim 1 wherein R is a $C_7$ to $C_{13}$ alkyl group.

8. A compound according to claim 7 wherein R is a $C_8$ to $C_{12}$ alkyl group.

9. A compound according to claim 8 wherein R is a $C_9$ alkyl group.

10. A compound according to claim 1 wherein R' and R" are each H.

11. A compound according to claim 1 wherein Q is O.

12. A compound according to claim 1 wherein X is O.

13. A compound according to claim 1 wherein Z is O.

14. A compound according to claim 1 wherein T is H.

15. A compound according to claim 1 wherein each of T, T', T" and T'" is H.

16. A compound according to claim 1 selected from the group consisting of:
3-[2',3'-dideoxy-ribo-β-D-furanosly]-6n-hexyl-2,3-dihydrofuro[2,3-d]pyrimidin-2-one;
3-[2',3'-dideoxy-ribo-β-D-furanosyl]-6-n-octyl-2,3-dihydrofuro[2,3-d]pyrimidin-2-one;
3-[2',3'-dideoxy-ribo-β-D-furanosyl]-6-n-nonyl-2,3-dihydrofuro[2,3-d]pyrimidin-2-one;
3-[2',3'-dideoxy-ribo-β-D-furanosyl]-6-[9-butyloxynonyl]-2,3-dihydrofuro[2,3-d]pyrimidin-2-one;
3-[2',3'-dideoxy-ribo-β-D-furanosyl]-6-[9-(4-chlorobutoxy)nonyl]-2,3-dihydrofuro[2,3-d]pyrimidin-2-one;
3-[2',3'-dideoxy-ribo-β-D-furanosyl]-6-n-decyl-2,3-dihydrofuro[2,3-d]pyrimidin-2-one;
3-[2',3'-dideoxy-ribo-β-D-furanosyl]-6-n-undecyl-2,3-dihydrofuro[2,3-d]pyrimidin-2-one;
3-[2', 3'-dideoxy-ribo-β-D-furanosyl]-6-n-dodecyl-2,3-dihydrofuro[2,3-d]pyrimidin-2-one;
3-[2', 3'-dideoxy-ribo-β-D-furanosyl]-6-n-tetradecyl-2,3-dihydrofuro[2,3-d]pyrimidin-2-one; and mixtures thereof.

17. A method for preparing a compound according to claim 1 comprising contacting a 5-halo nucleoside analogue with a terminal alkyne in the presence of a catalyst, or cyclizing a 5-alkynyl nucleoside in the presence of a catalyst.

18. A method of treatment of viral infection comprising administration to a patient in need of such treatment an effective dose of a compound according to claim 1.

19. A method according to claim 18 wherein the viral infection is a cytomegalo viral infection.

20. A pharmaceutical composition comprising a compound according to claim 1 in combination with a pharmaceutically acceptable excipient.

21. A method of preparing a pharmaceutical composition comprising the step of combining a compound according to claim 1 with a pharmaceutically acceptable excipient.

22. A compound according to claim 1 wherein $R_1$, $R^2$, $R^3$ and $R^4$ are each independently selected from the group consisting of straight chain alkyl moieties.

23. A compound according to claim 1 wherein $R^1$, $R^2$, $R^3$ and $R^4$ are each independently selected from the group consisting of $C_1$ to $C_5$ alkyl substituted with halogen.

24. A compound according to claim 5 wherein R is substituted with O-alkyl($C_4$), the $C_4$ alkyl moiety portion of which is optionally substituted with a halogen.

25. A compound according to claim 5 wherein R is substituted with O-alkyl($C_1$ to $C_5$) the $C_1$ to $C_5$ alkyl group portion of which is substituted with chlorine.

26. The method of claim 18 wherein the viral infection is cytomegalo viral infection.

* * * * *